United States Patent [19]

Okuyama

[11] Patent Number: 5,981,810
[45] Date of Patent: Nov. 9, 1999

[54] PROCESS FOR PREPARING 1,4-BUTANEDIOL

[75] Inventor: Manabu Okuyama, Mie, Japan

[73] Assignee: Mitsubishi Chemical Corporation, Tokyo, Japan

[21] Appl. No.: 09/094,701

[22] Filed: Jun. 15, 1998

[30] Foreign Application Priority Data

Jun. 16, 1997 [JP] Japan ..................................... 9-158593

[51] Int. Cl.[6] .................................................. C07C 29/78
[52] U.S. Cl. .......................... 568/868; 568/854; 568/923; 62/532
[58] Field of Search ..................................... 568/840, 852, 568/868, 923, 913, 856; 422/245.1; 62/532

[56] References Cited

U.S. PATENT DOCUMENTS

| | | | |
|---|---|---|---|
| 4,164,616 | 8/1979 | Childs | 568/858 |
| 4,294,998 | 10/1981 | Copelin | 568/868 |
| 5,546,763 | 8/1996 | Kikuchi et al. | 62/532 |

*Primary Examiner*—Shailendra Kumar
*Assistant Examiner*—Sreeni Padmanabhan
*Attorney, Agent, or Firm*—Oblon, Spivak, McClelland, Maier & Neustadt, P.C.

[57] ABSTRACT

This invention relates to a process for purifying crude 1,4-butanediol by melt crystallization and a process for preparing 1,4-butanediol by utilizing the purification process. 1,4-Butanediol is important as a material for synthesizing polyester resins, γ-butyrolactone, tetrahydrofuran, etc.

10 Claims, 4 Drawing Sheets

PROCESS FOR PREPARING 1,4-BUTANEDIOL

FIELD OF THE INVENTION

This invention relates to a process for purifying crude 1,4-butanediol by melt crystallization and a process for preparing 1,4-butanediol by utilizing the purification process. 1,4-Butanediol is important as a material for synthesizing polyester resins, γ-butyrolactone, tetrahydrofuran, etc.

BACKGROUND OF THE INVENTION

Known processes for preparing 1,4-butanediol include a butadiene process comprising acetoxylating butadiene with acetic acid and oxygen, hydrogenating the product to obtain diacetoxybutane, which is hydrolyzed to 1,4-butanediol (see JP-A-52-7909, JP-A-52-65208, JP-A-52-65209, and JP-A-52-133912, the term "JP-A" as used herein means an "unexamined published Japanese patent application"), a maleic anhydride process comprising hydrogenating maleic anhydride to produce 1,4-butanediol and γ-butyrolactone (see JP-A-2-233627), and an acetylene process comprising reacting acetylene and formaldehyde and hydrogenating the resulting 1,4-butenediol (see JP-A-52-91813).

The crude 1,4-butanediol obtained in these processes is usually purified by distillation, but it is difficult to achieve a high purity through simple distillation because the crude 1,4-butanediol contains impurities whose boiling points are extremely close to that of 1,4-butanediol and impurities which form azeotropic mixtures with 1,4-butanediol. Therefore, in order to increase the purity, large-sized equipment or high energy has been required for purification.

Of the impurities contained in crude 1,4-butanediol, 1,2-diacetoxybutane (hereinafter abbreviated as 12DAB), 1,4-diacetoxybutane (hereinafter abbreviated as 14DAB), 1,2-hydroxyacetoxybutane (hereinafter abbreviated as 12HAB), 1,4-hydroxyacetoxybutane (hereinafter abbreviated as 14HAB), dibutylene glycol (hereinafter abbreviated as DBG), 2-(4'-hydroxybutoxy)tetrahydrofuran (hereinafter abbreviated as BGTF), 2-(4'-oxobutoxy)tetrahydrofuran (hereinafter abbreviated as BDTF), and 1,4-di-(2'-tetrahydrofuroxy)butane (hereinafter abbreviated as BGDTF) cause coloring, cutting, and the like disadvantages when 1,4-butanediol is made into resins, fiber, etc.

In order to remove these impurities, JP-A-61-197534 proposes a method consisting of hydrogenation of crude 1,4-butanediol, and JP-A-6-172235 teaches a method comprising removing high-boiling point components by distillation followed by hydrogenation. According to these methods, however, the hydrogenation treatment must be followed by re-distillation to separate the impurities, requiring large-sized equipment or high energy for purification as mentioned above. Therefore, the methods are not always deemed efficient.

While not all the impurities present in crude 1,4-butanediol obtained by the conventional processes, such as a butadiene process, a maleic anhydride process, and an acetylene process, have been made clear as to the structure or the mechanism of formation, it has been proved that BGTF, BDTF, and BGDTF, especially BGTF, are re-produced during a distillation step. That is, as long as distillation is employed for the purification of crude 1,4-butanediol, there is a limit, of necessity, in removal of impurities, particularly BGTF. Continuous operation makes it more difficult to remove the impurities.

The outstanding problems of the process for preparing 1,4-butanediol are elaborated below, taking the butadiene process for instance.

The conventional butadiene process starts with reaction of butadiene with acetic acid and oxygen-containing gas, followed by hydrogenation to obtain diacetoxybutane (see FIG. 1). As shown in FIG. 2, the resulting diacetoxybutane is hydrolyzed, and acetic acid and water are distilled off from the liquid reaction mixture containing crude 1,4-butanediol (hydrolyzate) in a first distillation tower. Diacetoxybutane and hydroxyacetoxybutane are separated from the hydrolyzate in a second distillation tower. The resulting crude 1,4-butanediol is hydrogenated with hydrogen gas in the presence of a catalyst for hydrogenation. After tetrahydrofuran (hereinafter abbreviated as THF) is concentrated in a third distillation tower, high purity 1,4-butanediol is recovered from a fourth distillation tower as a side stream or a bottom.

Although this process provides 1,4-butanediol having a very high purity, it has many problems to be solved, such that diacetoxybutane and hydroxyacetoxybutane must be separated twice, the conditions of the separation are extremely severe, a considerable amount of THF is by-produced, and concentration of 1,4-butanediol or separation of high-boiling point impurities are conducted in three places.

A melt crystallization method is a technique used for increasing the purity of an organic compound having a high purity (e.g., 97 wt % purity) to a still higher level (e.g., 99.9 wt % purity). Industrial application of melt crystallization is found in the purification of bisphenol A and acrylic acid (see JP-A-7-163802 and JP-A-9-155101). Both the compounds have as low a viscosity as several centipoises at around their freezing point. On the other hand, 1,4-butanediol has as high a viscosity as 119 cp at around its freezing point (20° C.). Therefore, it has been regarded very difficult to apply melt crystallization to purification of crude 1,4-butanediol. In fact, as far as we know, there is no report on application of melt crystallization to purification of a crude organic compound like crude 1,4-butanediol which has a relatively high content of impurities whose freezing points are considerably lower than that of the target organic compound and has a high viscosity (about 120 cp) at about its freezing point.

SUMMARY OF THE INVENTION

An object of the present invention is to provide a process for purifying crude 1,4-butanediol containing various by-produced impurities easily, efficiently, and without requiring complicated steps.

Another object of the present invention is to provide a process for preparing 1,4-butanediol which affords high purity 1,4-butanediol efficiently.

As a result of extensive studies, the inventors of the present invention have found that melt crystallization is an efficient means for purifying crude 1,4-butanediol having a relatively high content of impurities whose freezing points are much lower than that of 1,4-butanediol and exhibiting a high viscosity at about its freezing point. They have also found that application of melt crystallization to the crude 1,4-butanediol obtained by hydrolysis of diacetoxybutane makes it possible to provide high purity 1,4-butanediol efficiently while reducing the load on the distillation tower. The present invention has been completed based on these findings.

The present invention provides (i) a process for purifying crude 1,4-butanediol comprising subjecting crude 1,4-butanediol containing impurities to melt crystallization.

The purification process of the present invention embraces the following preferred embodiments:

(ii) A process, wherein the melt crystallization is carried out by a wall melt crystallization method comprising the steps of (1) obtaining 1,4-butanediol crystals by running a crude 1,4-butanediol melt on a wall cooled to or below the freezing point of 1,4-butanediol and (2) recovering 1,4-butanediol as a crystal melt by heating the wall to or above the freezing point of 1,4-butanediol crystals.

(iii) A process, wherein the melt crystallization is carried out by a wall melt crystallization method comprising the steps of (1) obtaining 1,4-butanediol crystals by running a crude 1,4-butanediol melt on a wall cooled to or below the freezing point of 1,4-butanediol, (2) removing the residual crude 1,4-butanediol melt from the 1,4-butanediol crystals obtained in the step (1) and heating the wall to a temperature close to the freezing point of 1,4-butanediol crystals to sweat out the impurities in the 1,4-butanediol crystals, and (3) recovering 1,4-butanediol as a crystal melt by heating the wall to or above the freezing point of 1,4-butanediol crystals obtained in the step (2).

(iv) A process, wherein the thickness of the crystal layer formed in the step (1) is 1 to 20 mm.

(v) A process, wherein the crude 1,4-butanediol has a total content of impurities of 1% by weight or more.

(vi) A process, wherein the impurity is a compound having a freezing point of not higher than 0° C.

(vii) A process, wherein the impurity is at least one compound selected from 1,2-diacetoxybutane, 1,2-hydroxyacetoxybutane, 1,4-diacetoxybutane, 1,4-hydroxyacetoxybuitane, dibutylene glycol, 2-(4'-hydroxybutoxy)tetrahydrofuran, 2-(4'-oxobutoxy) tetrahydrofuran, 1,4-di-(2'-tetrahydrofuroxy)butane, 2-methyl-1,4-butanediol, γ-butyrolactone, 2-hydroxytetrahydrofuran, and 2-methylpentanediol.

The present invention also provides (viii) a process for preparing 1,4-butanediol comprising melt crystallizing crude 1,4-butanediol obtained by hydrolysis of diacetoxybutane in accordance with any of the above-described purification processes.

A preferred embodiment thereof is (ix) the process for preparing 1,4-butanediol comprises (1) removing low-boiling point impurities from crude 1,4-butanediol obtained by hydrolysis of diacetoxybutane, (2) melt crystallizing crude 1,4-butanediol obtained by the step (1) in accordance with any of the above-described purification processes to recover 1,4-butanediol crystal melt, (3) removing high-boiling point impurities from the mother liquor freed from the melt-crystallized 1,4-butanediol in the step (2), (4) hydrogenating the product obtained by the step (3), and (5) feeding the hydrogenation product back to the step (1).

Figure 1:
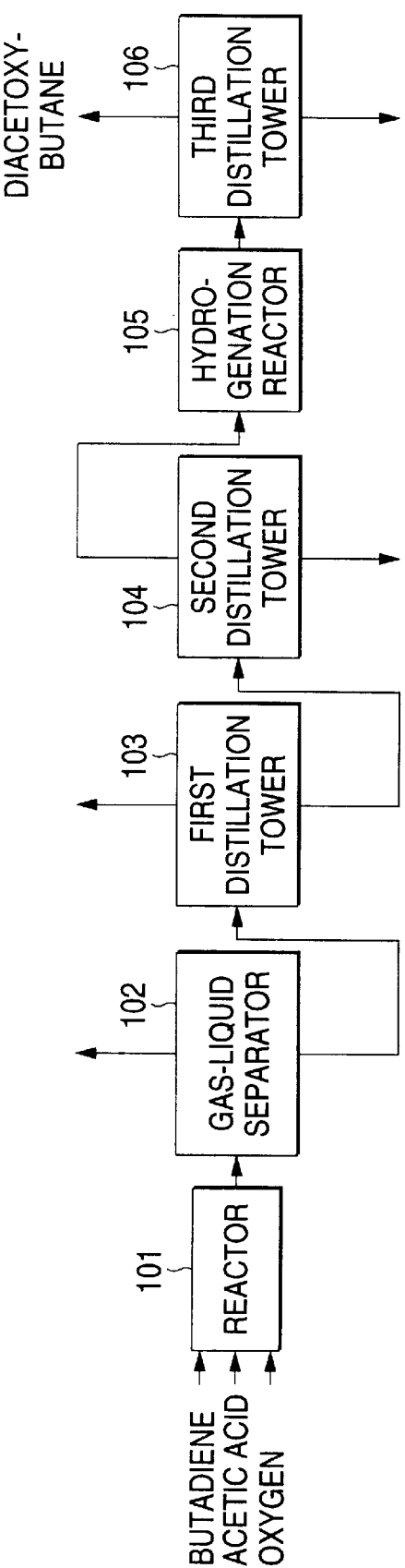
FIG. 1 is a flow chart of a process for producing diacetoxybutane.

Explanation of numerical symbols in the Figures
101 Reactor
102 Gas-liquid separator
103 First distillation tower
104 Second distillation tower
105 Hydrogenation reactor
106 Third distillation tower
201 Hydrolysis reactor
202 First distillation tower
203 Second distillation tower
204 Fifth distillation tower
205 First hydrogenation reactor
206 Second hydrogenation reactor
207 Gas/liquid separator
208 Third distillation tower
209 Fourth distillation tower
301 Hydrolysis reactor
302 First distillation tower
303 Second distillation tower
304 Melt crystallization apparatus
305 Third distillation tower
306 First hydrogenation reactor
401 Crystallizer
402 Water-circulating thermostat
V-0 Mother liquor storage tank
V-1, V-2, V-3 Storage tanks
V-5 Circulating tank

DETAILED DESCRIPTION OF THE INVENTION

Hereinafter, the present invention will be further described in detail.

(Crude 1,4-butanediol)

Crude 1,4-butanediol, which contains impurities and is to be purified by the purification process of the present invention (i.e., raw material), is not limited by the process of preparation. The purification process of the present invention is applicable to any crude 1,4-butanediol product obtained by known processes, such as a butadiene process, a maleic anhydride process, an acetylene process, a propylene process, and the like. For example, a product as obtained by these known processes and before purification or 1,4-butanediol as purified through rectification but still containing impurities can be treated as crude 1,4-butanediol in the present invention.

The impurities which are present in the crude 1,4-butanediol may be those forming a solid solution with 1,4-butanediol or those forming an azeotrope with 1,4-butanediol. The present invention is preferably applied to crude 1,4-butanediol containing the latter type of impurities. Such impurities include 12HAB, 12DAB, 14HAB (freezing point: −65° C.), 14DAB, DBG, BGTF, BDTF, BGDTF, 2-methyl-1,4-butanediol, γ-butyrolactone (freezing point: −44° C.), 2-hydroxytetrahydrofuran, and 2-methylpentanediol. The present invention is suited to purification of crude 1,4-butanediol containing 12HAB, 12DAB, 14HAB, 14DAB, DBG, BGTF, BDTF, and BGDTF, particularly crude 1,4-butanediol containing BGTF, BDTF, and BGDTF, especially BGTF-containing crude 1,4-butanediol.

The purification process of the present invention provides high purity 1,4-butanediol efficiently even if the starting crude 1,4-butanediol contains a relatively large amount of low-freezing point impurities. It is generally preferred to apply the process to removal of impurities having a freezing point of 0° C. or lower, still preferably −10° C. or lower, particularly preferably −30° C. or lower. The content of the impurities is not particularly limited. A suitable total content of impurities is 1% by weight or more and usually up to about 15% by weight, preferably about 1 to 10% by weight, still preferably about 2 to 10% by weight, particularly preferably about 3 to 10% by weight.

(Melt Crystallization Method)

While the method for carrying out melt crystallization is not particularly restricted, a method including at least a crystallizing operation is preferred. Examples of useful methods include (i) a wall melt crystallization method in which crystals are made to grow on a cooled wall, (ii) a method in which a melt is cooled to let crystals grow in liquid and, after removal of the mother liquor, impurities are sweat out of the crystals, and (iii) a method in which a melt is crystallized under pressure and, after removal of the mother liquor, impurities are sweat out of the crystals. The wall melt crystallization method is preferred of them.

The wall melt crystallization method basically comprises:

(1) a crystallizing step, in which a melt of crude 1,4-butanediol is run on a wall cooled to or below the freezing point of 1,4-butanediol to obtain crystals of 1,4-butadiene, and (2) a recovering step, in which the 1,4-butanediol crystals obtained in the crystallizing step are recovered as a crystal melt by heating the wall to or above the freezing point of 1,4-butanediol crystals.

The wall melt crystallization method preferably has an additional step of sweating out, comprising:

(1) a crystallizing step, in which a melt of crude 1,4-butanediol is run on a wall cooled to or below the freezing point of 1,4-butanediol to obtain crystals of 1,4-butadiene, (2) a sweating-out step, in which the 1,4-butanediol crystals obtained in the crystallizing step are freed of the residual crude 1,4-butanediol melt (mother liquor), and the wall is heated to a temperature close to the freezing point of 1,4-butanediol crystals to sweat out the impurities from the 1,4-butanediol crystals, and (3) a recovering step, in which the 1,4-butanediol crystals obtained by the sweating-out step are recovered as a crystal melt by heating the wall to or above the freezing point of 1,4-butanediol crystals.

In general, wall melt crystallization is achieved by the use of a crystallizing apparatus having a plate or a cylinder having smooth surfaces, on one side of which a crude liquid material is run while cooling the other side to precipitate crystals thereon. Wall melt crystallization is preferably carried out in a multi-stage system using a plurality of tanks. In this case, after a liquid material in a tank is treated, the mother liquor, the crystal melt and, if necessary, the sweat liquid are separately sent to the respective tanks, and the crystal melt is again subjected to melt crystallization.

The crystallizing apparatus may be a flat plate type, a cylinder type or any other types, but a flat plate type apparatus is preferred for effectively securing a heat transfer area. The method of melt crystallization using a flat plate type apparatus, which includes a sweating-out step if desired, will be described in detail. The apparatus is composed of a crystallizer, storage tanks, and feed pumps. The crystallizer has a stainless steel-made plate of 2 m in length, 1 m in width and 1 mm in thickness on which crystals are to be deposited (hereinafter sometimes referred to as a crystallizing plate). The crystallizing plate is set vertically, and the upper end is bent to form slant. The slant or an upright area extending from the upper end of the slant is connected to a liquid feeder from which a liquid material is run down on one side of the crystallizing plate in a thin film (hereinafter sometimes referred to as a crystallizing side). To increase the scale of production, the throughput can be increased by adding extra crystallizing plates.

On the other side of the crystallizing plate is provided a cooling medium feed pipe, from which a cooling medium having a temperature not higher than the freezing point of the liquid material is run down in a thin film on that side of the plate. The cooling medium feed pipe also serves as a heating medium feed pipe which supplies a heating medium having a temperature near the freezing point of the liquid material to the same side of the plate.

The liquid material is fed to the crystallizing side of the crystallizing plate by means of a feed pump, while a cooling medium is fed through a cooler by means of a separate feed pump and circulated through the cooling medium feed pipe. A heating medium is fed through a heater by means of a separate feed pump and circulated through the heating medium feed pipe (also serving as a cooling medium feed pipe).

The temperature control medium, i.e., a heating medium or a cooling medium, used in the crystallizing apparatus is not particularly limited, and any commonly employed medium capable of controlling temperature in a range of from about $-10°$ to $+30°$ C. can be used. For example, diols, such as ethylene glycol; lower alcohols, such as methyl alcohol and ethyl alcohol; water; and mixtures thereof are suitable.

The steps for carrying out melt crystallization will be explained in detail.

(1) Crystallizing Step

A crude 1,4-butanediol melt is run down on one side of the crystallizing plate in a film, while a cooling medium cooled to or below the freezing point of the 1,4-butanediol, i.e., 19 to $20°$ C. or lower is run on the other side of the plate in a film. The wall of crystallizing plate should be cooled to or below the freezing start point because crystals would not precipitate unless supercooled to some extent. The freezing start point, i.e., the temperature at which 1,4-butanediol melt starts freezing, varies depending on the purity and the feeding speed of the crude 1,4-butanediol melt. The freezing start point decreases with decreasing the purity of the crude 1,4-butanediol melt or with increasing the feeding speed of the crude 1,4-butanediol melt. However, it is desirable to slow down the crystal growth so as to minimize inclusion of impurities in the crystals during the growth. For this purpose, it is preferred that crystallization be initiated with a cooling medium having a temperature difference of about $8°$ C. at the greatest from the freezing point of the 1,4-butanediol (the temperature of the crystallizing plate wall is about $11°$ C.) and then the temperature of the cooling medium be gradually dropped to a point lower than the freezing point by about $15°$ C. as the crystals grow. Where melt crystallization is carried out in a multi-stage system, it is preferred that the temperature drop be slower in a later stage (for example, the rate of temperature drop in the second stage is made lower than that of the first stage). By this manipulation, the rate of crystal growth can be decreased as the stage proceeds, whereby crystals of higher purity can be obtained.

As the crude 1,4-butanediol melt runs on the crystallizing side of the crystallizing plate with a cooling medium running down on the other side, crystals of 1,4-butanediol are deposited on the crystallizing side. The temperature of the crude 1,4-butanediol melt to be fed is preferably higher than the freezing point of 1,4-butanediol by about $5°$ C., particularly about $1°$ C., at the highest in the initial stage. Since the surface of the crystal layer cannot be maintained at the initial temperature due to the heat of crystallization and reduction in heat transfer efficiency accompanying the increasing thickness of the crystal layer, the temperature rise on the crystal surface should be taken into consideration in gradually dropping the cooling temperature.

There is no upper limit to the flow rate of the crude 1,4-butanediol melt as far as a thin film can be formed. It is desirable that the flow rate be as high as possible so that the liquid film may not be cut and the heat transfer coefficient may be increased to improve the rate of treatment.

After a prescribed thickness of the 1,4-butanediol crystal layer is reached, the mother liquor is withdrawn from the circulating feed system. A thickness of the crystal layer is preferably from 1 to 20 mm, more preferably from 3 to 15 mm, and most preferably from 5 to 10 mm. If the crystal layer is too thin, it is liable to take in impurities. If it is too thick, the heat transfer efficiency decreases and the crystallizing time becomes longer, and moreover, when combined with sweating-out step, sweating-out time becomes longer, and the separation of the sweat liquid and the crystal layer becomes wrong.

(2) Sweating-Out Step

It is preferred for the 1,4-butanediol crystals obtained in the crystallizing step to be subjected to a sweating-out step prior to a recovering step.

A sweating-out step is the step of melting and removing a liquid having a high impurity concentration which has been incorporated among the crystals or adhered to the surface of the crystal layer thereby to further reduce the impurity content of the crystals. This step can be carried out by running a heating medium at a temperature close to the freezing point of the target pure substance, usually at (the freezing point of pure 1,4-butanediol ±5)° C., preferably (the freezing point of pure 1,4-butanediol ±3)° C., on the other side of the crystallizing plate in a thin film to partially melt the crystals. By this sweating-out step the impurity concentration in the crystals is further reduced.

The time of sweating is not particularly limited and is usually about 30 minutes. Because 1,4-butanediol has as high a viscosity as 77 cp at 25° C., the sweating time is preferably about 2 to 20 times as long as 30 minutes, i.e., 60 to 600 minutes.

(3) Recovering Step

The 1,4butanediol crystals obtained after the crystallizing step or, if desired, after the sweating-out step are heated to or above the freezing point of 1,4-butanediol crystals to recover 1,4-butanediol crystal melt. The heating is carried out by heating the temperature control medium in a heater to a prescribed temperature to make it a heating medium, and the heating medium is run down on the other side of the crystallizing plate. At the same time a 1,4-butanediol crystal melt which has previously been obtained is heated and run down on the crystallizing side (i.e., surface of crystal layer) of the crystallizing plate. Thus, the 1,4-butanediol crystal layer is heated from both sides thereof and thereby melted in a short time.

The above-described crystallizing step, sweating-out step, and recovering step provide 1,4-butanediol having a high purity. Higher purity 1,4-butanediol can be obtained by again subjecting the resulting 1,4-butanediol to melt crystallization. Accordingly, 1,4-butanediol having an extremely high purity could be obtained by repeating the melt crystallizing steps in a multi-stage system.

Figure 4:
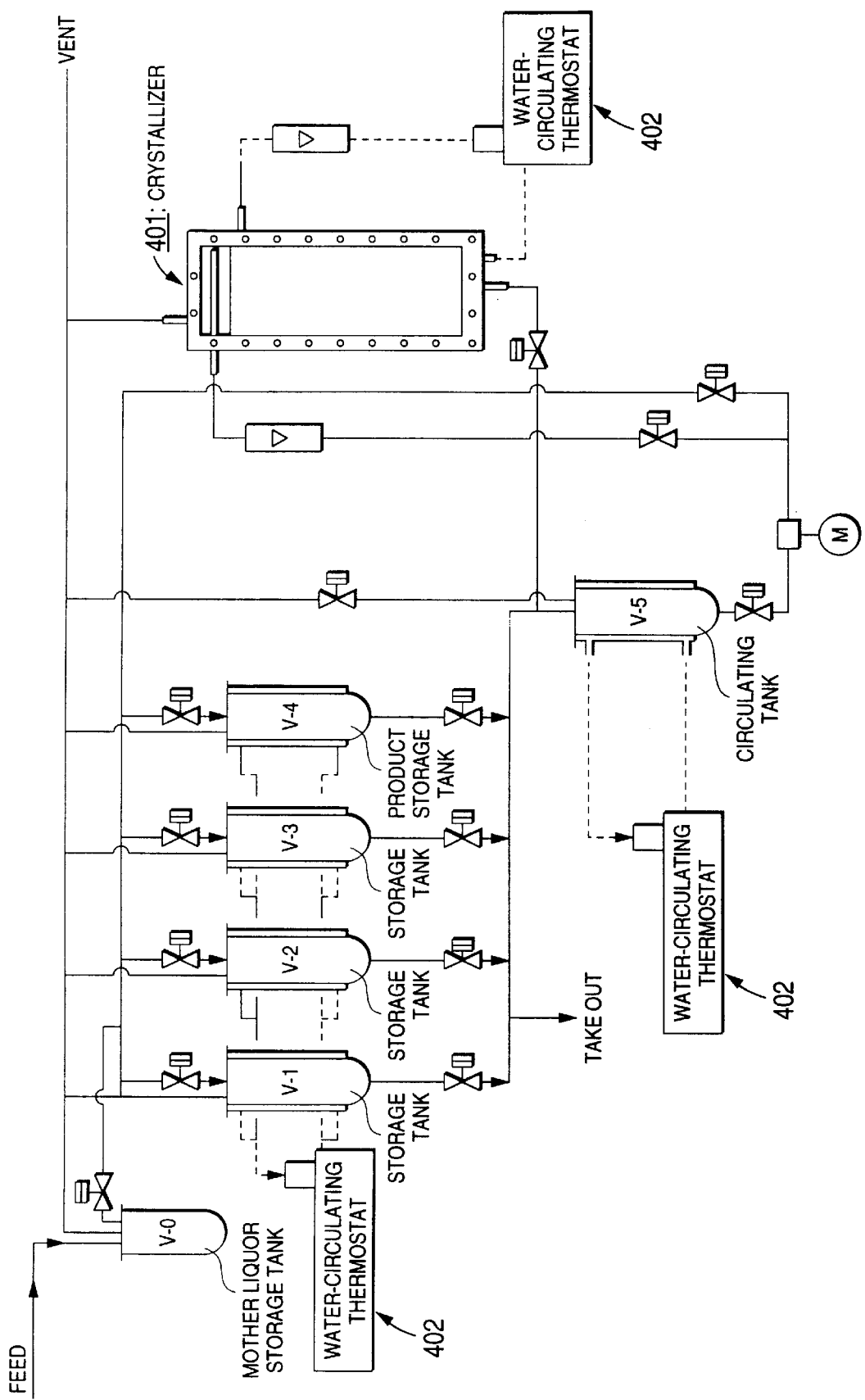
FIG. 4 illustrates an example of a melt crystallizing apparatus for carrying out the process of the present invention.

FIG. 4 schematically illustrates an example of a melt crystallization apparatus for carrying out two-stage melt crystallization. V-0 to V-4 are each a storage tank, V-5 is a circulating tank, and V-4 is a product storage tank wherein the final product 1,4-butanediol is temporarily stored. V-0 is a mother liquor storage tank wherein the mother liquor resulting from crystallization of a liquid material having the lowest purity, i.e., the mother liquor obtained by crystallizing the liquid material in the tank V-1, is temporarily stored. The liquid material of the tank V-2 is sent to the circulating tank V-5 and passed through a crystallizer 1 to precipitate 1,4-butanediol crystals in the crystallizer 1 (crystallizing step).

The non-crystallized residual liquid (mother liquor) remaining in the circulating tank V-5 is sent to the tank V-1. Subsequently, the 1,4-butanediol crystals in the crystallizer 1 are subjected to sweating-out, and the sweat liquid is stored in the tank V-2 (sweating-out step). The purified liquid of the first stage obtained by melting 1,4-butanediol crystal in the crystallizer 1 is delivered to the tank V-3 (recovering step).

The liquid in the tank V-3 is sent to the circulating tank V-5 and circulated through the crystallizer 1 to precipitate 1,4-butanediol crystals in the crystallizer (crystallizing step). Accompanying the crystallizing step, sweating-out step and recovering step are conducted, The resulting mother liquor, sweat liquid, and purified liquid are sent are shifted one by one. That is, the melt in the tank V-3 is sent to the circulating tank V-5 and crystallized in the crystallizer 1, and the mother liquor and sweat liquid from the crystallizer 1 are stored in the tanks V-2 and V-3, respectively, while the melted crystals are recovered in the product storage tank V-4.

After the crystallizing operation for the melt in the tank V-3, the melt in the tank V-1 (the mother liquor obtained after the crystallizing operation for the melt of the tank V-2) is subjected to melt crystallization in quite the same manner as the above-mentioned operation, and the resulting mother liquor and sweat liquid are sent to the external mother liquor storage tank V-0 and the tank V-1, respectively. The mother liquor in the tank V-0 is returned to a distillation tower. The melted liquid recovered from crystallizer 1 is stored in the tank V-2. One cycle of the purification is thus completed.

Preferably, at the recovering step, a 1,4-butanediol crystal melt which has previously been obtained runs down on the surface of crystal layer. Thus, the 1,4-butanediol crystal layer is heated from both sides thereof and thereby melted in a short time.

As previously stated, the crude 1,4-butanediol to be purified by the process of the present invention is not limited by the process of production, but the one obtained by a butadiene process is particularly suitable. Thus, in another aspect of the present invention there is provided a process for preparing 1,4-butanediol comprising melt crystallizing crude 1,4-butanediol obtained by a butadiene process, i.e., hydrolysis of diacetoxybutane.

(Process for preparing 1,4-butanediol)

In the process for preparing 1,4-butanediol according to the present invention, the crude 1,4-butanediol is a reaction product obtained by hydrolyzing diacetoxybutane. The diacetoxybutane is usually obtained by hydrogenation of diacetoxybutene that is obtained by reacting butadiene, acetic acid, and oxygen in the presence of a palladium catalyst (see JP-B-55-45051, JP-B-55-16489, and JP-B-55-17016, the term "JP-B" as used herein means an "examined published Japanese patent application"). A flow chart of the diacetoxybutane preparation is shown in FIG. 1.

The diacetoxybutane to be hydrolyzed includes not only one consisting mainly of 1,4-diacetoxybutane but an isomeric mixture comprising 1,4-diacetoxybutane and 1,2-diacetoxybutane, 1,3-diacetoxybutane, etc. and one additionally containing monohydroxyacetoxybutane, the composition depending on the production and purification steps. In some cases, a mixture of 1,4-diacetoxybutane, 1,4-monohydroxyacetoxybutane, and 1,4-butanediol, which is obtained by removing water and acetic acid after some progress of hydrolysis reaction, can also be used.

The hydrolysis reaction is preferably carried out using a cationic exchange resin as a catalyst for achieving an accelerated rate of hydrolysis and reducing by-production of THF. Sulfonic acid type strongly acidic cation exchange resins comprising a styrene-divinylbenzene copolymer are preferred, which may be of either a gel type or a porous type. Examples of sulfonic acid type strongly acidic cation exchange resins are SK1B, SK104, SK106, SK110, and SK112 (of gel type, all produced by Mitsubishi Chemical Corporation) and PK208, PK216, PK228, RCP160H, RCP170H, and RCP145H (of porous type, all produced by Mitsubishi Chemical Corporation).

The hydrolysis is usually performed at 30 to 110° C., preferably 40 to 90° C. The reaction pressure is not particularly limited and usually ranges from atmospheric pressure to 10 kg/cm² (0.1 to 1.08 MPa). Acting as not only a reactant but a solvent, water is used in an amount more than a stoichiometric amount usually ranging from 2 to 100 mol, preferably 4 to 50 mol, per mole of diacetoxybutane.

While various reaction modes are possible, it is a generally followed practice to run diacetoxybutane and water through a fixed bed packed with an acidic cation exchange resin.

Figure 3:
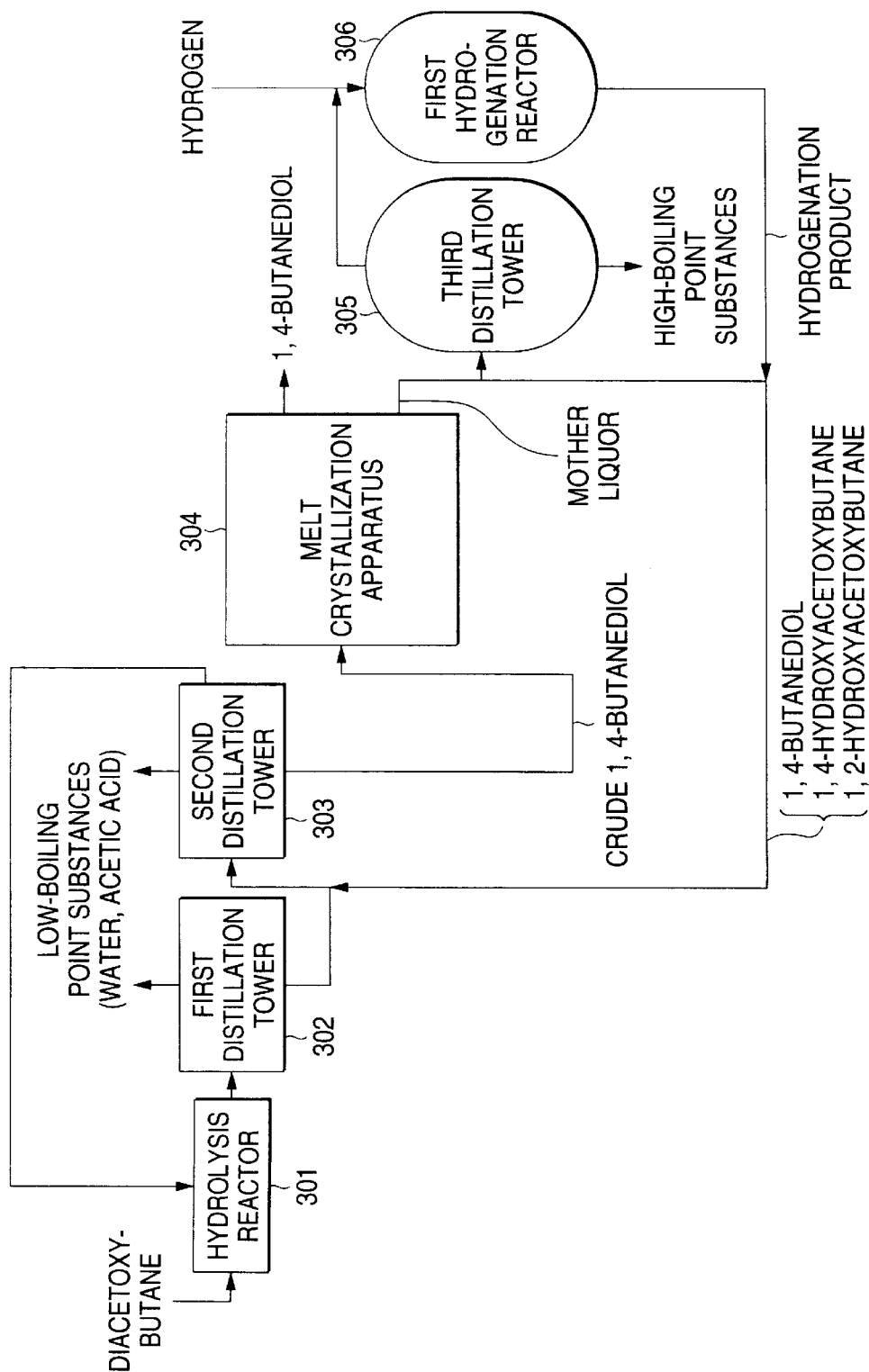
FIG. 3 is a flow chart of an example of the process for preparing 1,4-butanediol from diacetoxybutane according to the present invention.

The resulting hydrolysis reaction mixture is usually distilled to obtain crude 1,4-butanediol free from low-boiling point components and high-boiling point components. To carry out distillation, well-known techniques, such as the method disclosed in JP-A-6-172235, are employable, but where the process of the present invention is followed, the distillation conditions can be made milder than those adopted in conventional processes for preparing 1,4-butanediol. In addition, unlike the conventional processes, the hydrogenation step, which has been conducted to reduce the impurities, is not always necessary. More specifically, as shown in FIG. 3, the reaction mixture obtained by hydrolysis of diacetoxybutane is fed to a distillation tower to remove low-boiling point components, such as water, acetic acid, 12HAB, and 14HAB, and the residual hydrolysis product is discharged from the bottom or the side stream to obtain crude 1,4-butanediol. The low-boiling point components are preferably removed by using two or more distillation towers. In FIG. 3, for example, water and acetic acid are distilled off in a first distillation tower 302, and 12HAB, 14HAB, etc. are distilled off in a second distillation tower 303.

The crude 1,4-butanediol withdrawn from the bottom or the side stream of the distillation tower is subjected to melt crystallization as such in accordance with the aforesaid purification process. Melt crystallization is preferably carried out by -the method comprising (1) a crystallizing step and (3) a recovering step and, if desired, (2) a sweating-out step prior to the recovery step.

In the present invention, it is preferred that the crude 1,4-butanediol withdrawn from the distillation tower be subjected to melt crystallization without being hydrogenated and that the mother liquor from the crystallizing step be fed to another distillation tower to remove high-boiling point impurities such as dibutyleneglycol, dibutyleneglycol monoacetate, dibutyleneglycol diacetate, tributyleneglycol, tributhyleneglycol monoacetate, tributyleneglycol diacetate, and others, subjected to hydrogenation, and then returned to the previous distillation tower for removal of low-boiling point components (see FIG. 3). This embodiment excludes the necessity of the step for THF concentration as in conventional processes (e.g., the third and fourth distillation towers in FIG. 2) and also makes it feasible to relax the distillation conditions for separation between 1,4-butanediol and hydroxyacetoxybutane. According to the conventional purification process using a distillation method shown in FIG. 2, the contents of 14HAB, 12HAB, and BGTF of the crude 1,4-butanediol obtained from the bottom of the first distillation tower should be reduced to 0.5 wt % or less, 0.1 wt % or less, and 2.0 wt % or less, respectively. To the contrary, where melt crystallizing purification is adopted, the upper limits of 14HAB, 12HAB, and BGTF contents of the crude 1,4-butanediol from the second distillation tower can be lowered to 2 wt % or less, 0.4 wt % or less, and 8 wt % or less, respectively, and yet it is possible to obtain 1,4-butanediol equal, in purity, to that obtained by the conventional distillation method.

More specifically, in the conventional distillation method (FIG. 2) the second distillation tower 203 is generally required to have 50 to 150 plates in terms of a number of theoretical plates and be operated under a tower top pressure of 100 to 400 mmHg, at a tower top temperature of 150 to 250° C., preferably 180 to 230° C., and at a reflux ratio of 10 to 200, preferably 20 to 100. In the present invention, on the other hand, the distillation tower 303 (FIG. 3), for example, is operated with 25 to 75 theoretical plates, and at a reflux ratio of 5 to 100, preferably 10 to 50, which are the half of those used in the conventional distillation method.

The present invention will now be illustrated in greater detail with reference to Examples, but it should be understood that the present invention is not construed as being limited thereto. Unless otherwise noted, all the parts and percents are given by weight, and all the analytical values are those measured by gas chromatography after 5 days' continuous running when a steady state was reached.

REFERENCE EXAMPLE 1

To a reactor 101 shown in FIG. 1 were fed 170 part/hr of butadiene, 3000 part/hr of acetic acid containing 0.8% of 1,4-hydroxyacetoxybutane and 0.6% of 1,2-hydroxyacetoxybutane as impurities, and 530 part/hr of oxygen, and the mixture was reacted at 100° C. and 9 MPa in the presence of a catalyst comprising activated carbon having supported thereon 3% of palladium and 0.6% of tellurium. The reaction mixture was freed from gas in a gas-liquid separator 102 to obtain a reaction product containing 12.5% of 1,4-diacetoxybutene.

The reaction product was fed to a first distillation tower 103 at a rate of 3100 part/hr to remove the most part of water and acetic acid at a rate of 2500 part/hr as a distillate while discharging the bottom containing 74.8% of 1,4-diacetoxybutene at a rate of 580 part/hr.

The bottom was fed to a second distillation tower 104 with 20 plates and distilled under a tower top pressure of 2.7 kPa and at a reflux ratio of 0.5 to obtain a distillate containing 75.5% of 1,4-diacetoxybutene at a rate of 550 part/hr.

The resulting diacetoxybutene fraction was sent to a hydrogenation reactor 105 packed with a palladium catalyst and a ruthenium catalyst and hydrogenated in a hydrogen stream under a reaction pressure of 5 MPa and at a temperature of 70° C. to obtain a reaction mixture containing 75.6% of 1,4-diacetoxybutane.

The reaction mixture was freed from gas, fed to a third distillation tower 106 with 20 plates at a rate of 550 part/hr, and distilled under a tower top pressure of 2.7 kPa and at a reflux ratio of 0.5 to correct 520 part/hr of a distillate having the composition shown in Table 1 below (1,4-diacetoxybutane content: 75.9%) from the top.

The resulting 1,4-diacetoxybutane-containing liquid and a 28% aqueous solution of acetic acid were fed to a reactor packed with 100 l of a cation exchange resin SK1B (produced by Mitsubishi Chemical Corporation) at a rate of 520 part/hr and 250 part/hr, respectively, to effect hydrolysis at 50° C. The composition of the resulting hydrolyzate, except for water, is shown in Table 1.

TABLE 1

| Component | Before Hydrolysis (%) | After Hydrolysis (%) |
| --- | --- | --- |
| 1,4-Diacetoxybutane | 75.9 | 8.0 |
| 1,4-Hydroxyacetoxybutane | 5.2 | 32.5 |
| 1,4-Butanediol | 0.5 | 27.8 |
| 1,2-Diacetoxybutane | 8.3 | 0.7 |
| 1,2-Hydroxyacetoxybutane | 4.3 | 1.8 |
| 1,2-Butanediol | 0.2 | 4.7 |
| Acetic acid | 2.2 | 20.4 |
| Others | 3.4 | 4.1 |

The hydrolyzate was distilled in the first distillation tower 302 shown in FIG. 3, which was a packed tower made of SUS316 having an inner diameter of 200 mm and packed with SUS316-made Raschig rings to a height of 3000 mm. The liquid was fed to a feed opening 500 mm below the top of the packed bed and distilled at a tower top pressure of 70 mmHg, at a reflux ratio of 0.5, and at a tower bottom temperature of 160° C. Water, acetic acid, and a trace amount of other low-boiling point substances were distilled off, and the bottom was sent to the second distillation tower 303.

The second distillation tower was a packed tower made of SUS304 having an inner diameter of 100 mm and packed with SUS304-made McMahon packing to a height of 5000 mm. The tower had an outlet for a side stream 1000 mm below the top of the packed bed, a liquid feed opening 1000 mm below the side stream outlet, and an outlet for steam 1000 mm below the feed opening. The tower was operated under a tower top pressure of 230 mmHg, at a reflux ratio of 30, and at a bottom temperature of 200° C. and a top temperature of 155° C.

From the top of the tower was distilled off a fraction comprising 9.5% of 1,2-diacetoxybutane, 25.2% of 1,2-dihydroxyacetoxybutane, and 65.3% of 1,2-butanediol. From the side stream was obtained a fraction comprising 0.4% of 1,2-diacetoxybutane, 0.9% of 1,2-hydroxyacetoxybutane, 2.4% of 1,2-butanediol, 15.9% of 1,4-diacetoxybutane, 64.1% of 1,4-hydroxyacetoxybutane, and 11.4% of 1,4-butanediol. The side stream fraction was returned to the hydrolysis reaction zone as a part of the reaction material. Crude 1,4-butanediol (comprising 94.0% of 1,4-butanediol, 0.02% of 14HAB, and 0.48% of BGTF) was obtained as a bottom liquid from the distillation tower 303.

EXAMPLE 1

(1) The crude 1,4-butanediol obtained in Reference Example 1 was crystallized through two stages by the use of a crystallizing apparatus shown in FIG. 4, in which a vertical blade type crystallizer was used as shown. The stainless steel-made crystallizing plate had a width of 200 mm and a height of 600 mm. The front wall and the ceiling of the crystallizer housing were made of a clear acrylic resin so that the crystallizing plate could be seen through. A 30 to 40% aqueous solution of ethylene glycol was used as a temperature control medium.

(2) The crude 1,4-butanediol (500 g) was supplied to a storage tank V-2 and from there forwarded once to a circulating tank V-5 and then to a crystallizer 1. The liquid material was circulated through the crystallizer under predetermined conditions to crystallize a 450 g portion of the liquid material. The residual 50 g portion, i.e., the mother liquor was sent to a storage tank V-1. Thereafter the crystals were made to sweat for 2 hours to generate 200 g of a sweat liquid, which was transferred to the storage tank V-2. The first stage crystals were melted and transferred to a storage tank V-3.

(3) The melt in the storage tank V-3 was sent to the circulating tank V-5 and then circulated to the crystallizer 1. In the same manner as described above, the mother liquor (10 g) was returned to the storage tank V-2, the sweat liquid (165 g) to the storage tank V-3, and the purified melt (75 g) to a storage tank V-4 (product tank).

(4) The purified melt in the storage tank V-4 had a 1,4-butanediol purity of about 97.7% and a BGTF content of 0.19%.

EXAMPLE 2

The crude 1,4-butanediol obtained in Reference Example 1 was crystallized through two stages in the same manner as in Example 1 with the following exception.

After 450 g of the liquid material was crystallized, and 50 g of the mother liquor was sent to the storage tank V-1, the crystals were made to sweat over a period of about 4 hours, and the resulting sweat liquid (200 g) was sent to the storage tank V-2, and the first stage crystal melt was sent to the storage tank V-3.

The melt in the storage tank V-3 was sent to the circulating tank V-5 and then circulated to the crystallizer 1. In the same manner as the first stage crystallizing step, the mother liquor (10 g), the sweat liquid (185 g), and the purified melt (15 g) were delivered to the storage tanks V-2, V-3, and V-4, respectively.

The purified melt in the storage tank V-4 had a 1,4-butanediol purity of about 99.7% and a BGTF content of 0.08%.

COMPARATIVE EXAMPLE 1

Figure 2:
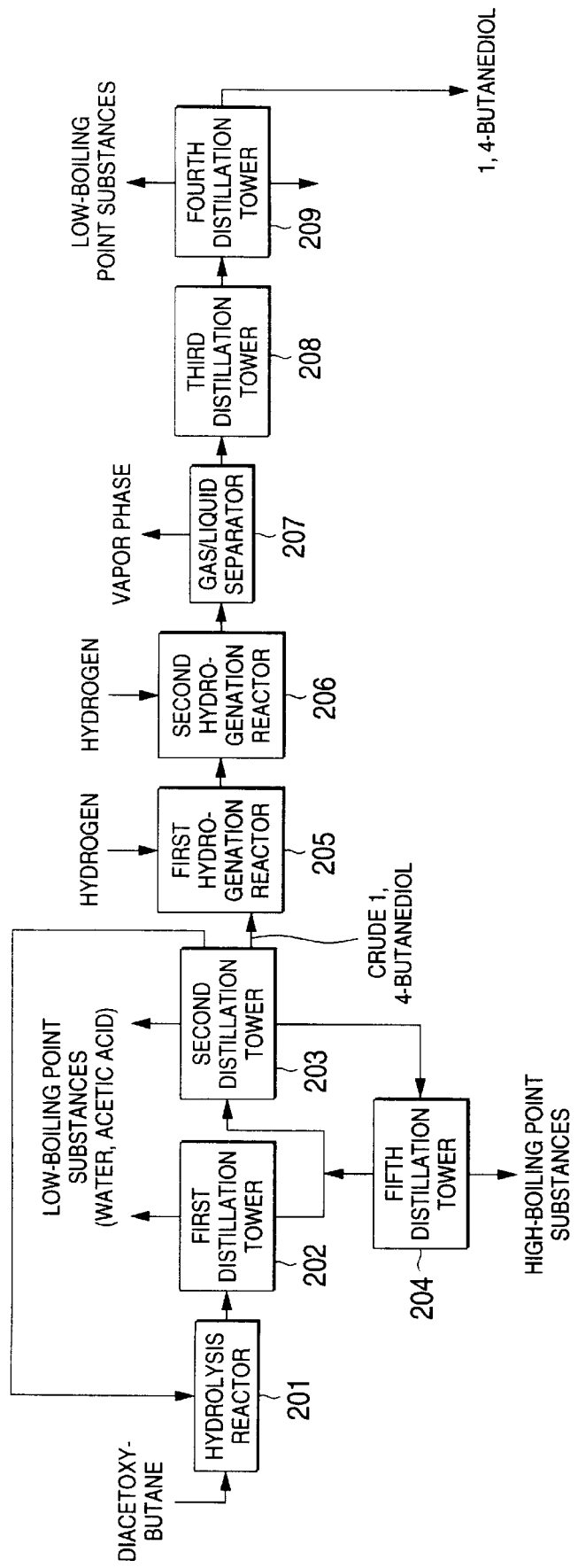
FIG. 2 is a flow chart of a conventional process for producing 1,4-butanediol from diacetoxybutane.

1,4-Butanediol was produced starting with diacetoxybutane in accordance with a conventional distillation method as shown in FIG. 2.

The crude 1,4-butanediol obtained from the side stream of the second distillation tower 203 shown in FIG. 2 comprised 97.0% of 1,4-butanediol, 0.5% of 14HAB, and 2.0% of BGTF. The product recovered from the fourth distillation tower 209 of FIG. 2 after 1000-hours' continuous running had a 1,4-butanediol purity of 99.7% and a BGTF content of 0.25%.

According to the present invention, various impurities by-produced in the production process can be removed simply, easily and efficiently without involving complicated steps by melt crystallization purification. In particular, BGTF that is difficult to separate by distillation can be removed efficiently.

Where the purification process of the present to invention is applied to the crude 1,4-butanediol obtained by hydrolysis of diacetoxybutane, the load in the distillation step and the hydrogenation step can be reduced, and high purity 1,4-butanediol can be prepared efficiently.

While the invention has been described in detail and with reference to specific embodiments thereof, it will be apparent to one skilled in the art that various changes and modifications can be made therein without departing from the spirit and scope thereof.

This application is based on Japanese patent application Hei-9-158593, filed on Jun. 16, 1997, incorporated herein by reference.

What is claimed is:

1. A process for purifying crude 1,4-butanediol comprising subjecting crude 1,4-butanediol containing impurities to melt crystallization.

2. A process according to claim 1, wherein said melt crystallization is carried out by a wall melt crystallization method comprising the steps of (1) obtaining 1,4-butanediol crystals by running a crude 1,4-butanediol melt on a wall cooled to or below the freezing point of 1,4-butanediol and (2) recovering 1,4-butanediol as a crystal melt by heating the wall to or above the freezing point of 1,4-butanediol crystals.

3. A process according to claim 1, wherein said melt crystallization is carried out by a wall melt crystallization method comprising the steps of (1) obtaining 1,4-butanediol crystals by running a crude 1,4-butanediol melt on a wall cooled to or below the freezing point of 1,4-butanediol, (2) removing the residual crude 1,4-butanediol melt from the 1,4-butanediol crystals obtained in the step (1) and heating the wall to a temperature close to the freezing point of 1,4-butanediol crystals to sweat out the impurities in the 1,4-butanediol crystals, and (3) recovering 1,4-butanediol as a crystal melt by heating the wall to or above the freezing point of 1,4-butanediol crystals obtained in the step (2).

4. A process according to claim 2, wherein the thickness of the crystal layer formed in the step (1) is 1 to 20 mm.

5. A process according to claim 3, wherein the thickness of the crystal layer formed in the step (1) is 1 to 20 mm.

6. A process according to any one of claims 1 to 5, wherein the crude 1,4-butanediol has a total content of impurities of 1% by weight or more.

7. A process according to any one of claims 1 to 5, wherein the impurity is a compound having a freezing point of not higher than 0° C.

8. A process according to any one of claims 1 to 5, wherein the impurity is at least one compound selected from 1,2-diacetoxybutane, 1,2-hydroxyacetoxybutane, 1,4-diacetoxybutane, 1,4-hydroxyacetoxybutane, dibutylene glycol, 2-(4'-hydroxybutoxy)tetrahydrofuran, 2-(4'-oxobutoxy) tetrahydrofuran, 1,4-di-(2'-tetrahydrofuroxy) butane, 2-methyl-1,4-butanediol, γ-butyrolactone, 2-hydroxytetrahydrofuran, and 2-methylpentanediol.

9. A process for purifying 1,4-butanediol comprising melt crystallizing crude 1,4-butanediol obtained by hydrolysis of diacetoxybutane.

10. A process for preparing 1,4-butanediol comprising
   (1) removing low-boiling point impurities from crude 1,4-butanediol obtained by hydrolysis of diacetoxybutane,
   (2) melt crystallizing crude 1,4-butanediol obtained by the step (1) to recover 1,4-butanediol crystal melt,
   (3) removing high-boiling point impurities from the mother liquor freed from the melt-crystallized 1,4-butanediol in the step (2),
   (4) hydrogenating the product obtained by the step (3), and
   (5) feeding the hydrogenation product back to the step (1).

* * * * *